United States Patent
Palmer et al.

(10) Patent No.: US 7,004,956 B2
(45) Date of Patent: Feb. 28, 2006

(54) EMBOLIC BASKET

(75) Inventors: Olin Palmer, Mountain View, CA (US); Christopher T. Shen, Stanford, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 220 days.

(21) Appl. No.: 10/423,300

(22) Filed: Apr. 25, 2003

(65) Prior Publication Data

US 2003/0204202 A1 Oct. 30, 2003

Related U.S. Application Data

(60) Division of application No. 09/939,205, filed on Aug. 24, 2001, now Pat. No. 6,575,997, which is a continuation-in-part of application No. 09/469,431, filed on Dec. 23, 1999, now Pat. No. 6,402,771.

(51) Int. Cl.
*A61M 29/00* (2006.01)
(52) U.S. Cl. ..................................... 606/200
(58) Field of Classification Search ................ 606/200, 606/159, 113, 114, 127; 623/1.15, 1.16
See application file for complete search history.

(56) References Cited

U.S. PATENT DOCUMENTS

| | | |
|---|---|---|
| 2,943,626 A | 7/1960 | Dormia |
| 4,347,846 A | 9/1982 | Dormia |
| 4,611,594 A | 9/1986 | Grayhack et al. |
| 4,619,246 A | 10/1986 | Molgaard-Nielsen et al. |
| 4,865,017 A | 9/1989 | Shinozuka |
| 4,873,978 A | 10/1989 | Ginsburg |
| 4,969,891 A | 11/1990 | Gewertz |
| 4,990,156 A | 2/1991 | Lefebvre |
| 4,998,539 A | 3/1991 | Delsanti |
| 5,152,777 A | 10/1992 | Goldberg et al. |
| 5,171,233 A | 12/1992 | Amplatz et al. |
| 5,192,286 A | 3/1993 | Phan et al. |
| 5,234,458 A | 8/1993 | Metais |
| 5,330,482 A | 7/1994 | Gibbs et al. |
| 5,383,887 A | 1/1995 | Nadal |
| 5,486,183 A | 1/1996 | Middleman et al. |
| 5,496,330 A | 3/1996 | Bates et al. |
| 5,509,923 A | 4/1996 | Middleman et al. |
| 5,549,626 A | 8/1996 | Miller et al. |
| 5,601,572 A | 2/1997 | Middleman et al. |
| 5,681,347 A | 10/1997 | Cathcart et al. |
| 5,695,518 A | 12/1997 | Laerum |
| 5,720,754 A | 2/1998 | Middleman et al. |
| 5,720,764 A | 2/1998 | Naderlinger |
| 5,792,156 A | 8/1998 | Perouse |
| 5,810,874 A | 9/1998 | Lefebvre |
| 5,820,628 A | 10/1998 | Middleman et al. |
| 5,895,398 A | 4/1999 | Wensel et al. |
| 5,902,263 A | 5/1999 | Patterson et al. |
| 5,904,690 A | 5/1999 | Middleman et al. |
| 6,053,932 A | 4/2000 | Daniel et al. |
| 6,168,603 B1 | 1/2001 | Leslie et al. |
| 6,443,972 B1 * | 9/2002 | Bosma et al. ................ 606/200 |
| 6,551,342 B1 * | 4/2003 | Shen et al. .................. 606/200 |

* cited by examiner

*Primary Examiner*—Kevin T. Truong
(74) *Attorney, Agent, or Firm*—Fulwider Patton LLP

(57) ABSTRACT

An intravascular basket device for use in capturing either naturally occurring or foreign debris found in blood vessels or other regions of the body. The basket device is fabricated from a tube and includes a mid-section having at least one ring configured in an alternating V-pattern. The basket device specifically embodies structure that provides enhanced radial opening and angular resistance to collapse.

21 Claims, 7 Drawing Sheets

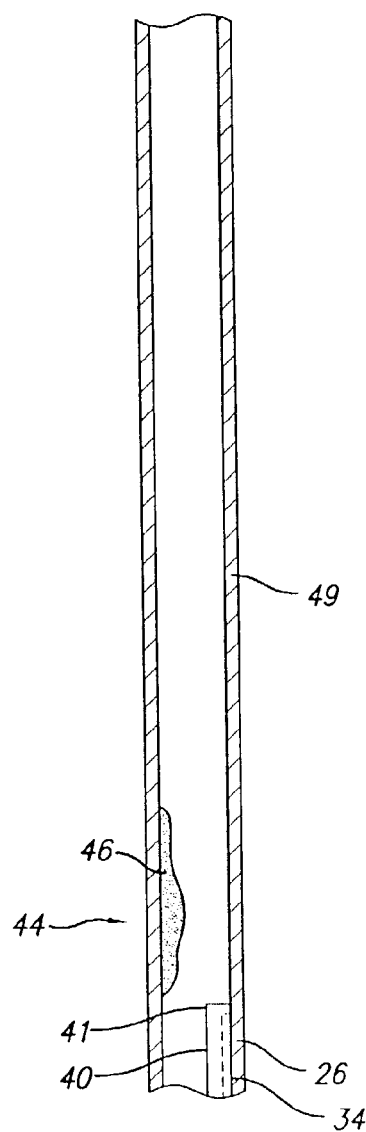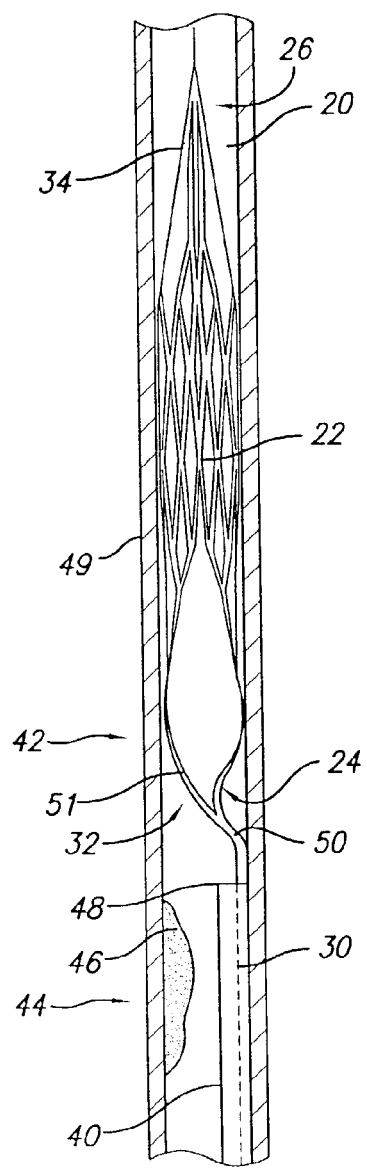

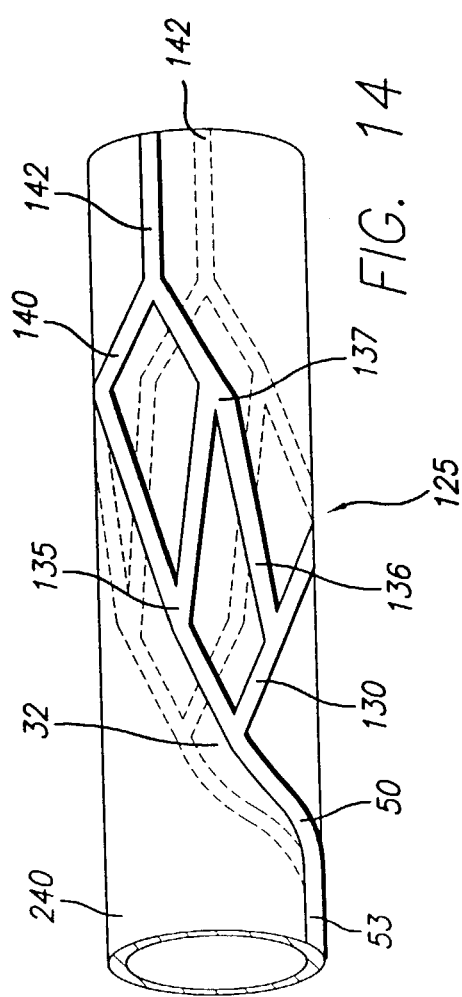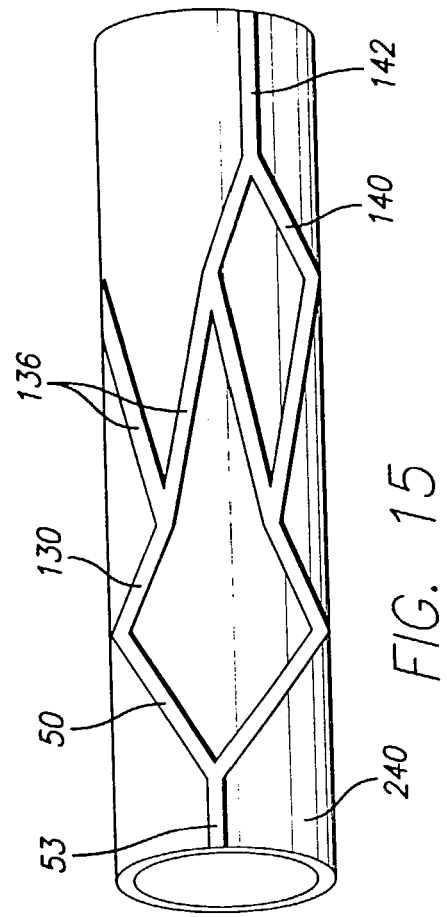

EMBOLIC BASKET

CROSS-REFERENCES TO RELATED APPLICATIONS

This application is a divisional of U.S. application Ser. No. 09/939,205, filed Aug. 24, 2001 now U.S. Pat. No. 6,575,997, which is a continuation-in-part of application Ser. No. 09/469,431, filed Dec. 23, 1999 now U.S. Pat No. 6,402,771. The content of that application is hereby incorporated herein by reference.

BACKGROUND OF THE INVENTION

The present invention relates generally to intravascular devices and systems and more particularly, basket devices which can be used to capture embolic material or thrombi found in blood vessels.

The intravascular basket device and system of the present invention is particularly useful when performing balloon angioplasty, stenting procedures, laser angioplasty or atherectomy in critical vessels where the release of embolic debris into the bloodstream can occlude the flow of oxygenated blood to the brain or other vital organs, which can cause devastating consequences to the patient. The basket device is also suited for the removal of clots adhering to vessel walls. The device is also suitable for removal of misplaced coils or other foreign material. While the basket device and system of the present invention is particularly useful in the cerebral vasculature and neurovasculature, the invention can be used in conjunction with any vascular interventional procedure in which there is an embolic risk. Additionally, it can be used in any region of the body where removal of debris or foreign material is indicated. Having a patterned body cut from a single tube element, the basket device allows for an enhanced radial opening into the basket body that provides for greater ease of embolic capture. Additionally the patterned body embodies greater stability during use by resisting the natural tendency to collapse as seen in most prior art snares during a typical operation.

A variety of non-surgical interventional procedures have been developed over the years for opening stenosed or occluded blood vessels in a patient caused by the build-up of plaque or other substances on the wall of the blood vessel. Such procedures usually involve the remote introduction of the interventional device into the lumen of the artery, usually through a catheter. In typical carotid PTA procedures, a guiding catheter or sheath is percutaneously introduced into the cardiovascular system of a patient through the femoral artery and advanced, for example, through the vasculature until the distal end of the guiding catheter is in the common carotid artery. A guidewire and a dilatation catheter having a balloon on the distal end are introduced through the guiding catheter with the guidewire sliding within the dilatation catheter. The guidewire is first advanced out of the guiding catheter into the patient's carotid vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. A first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site. A second type of stent is a self-expanding stent formed from, for example, shape memory metals or super-elastic nickel-titanum (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

The above minimally invasive interventional procedures, when successful, avoid the necessity of major surgical operations. However, there is one common problem which can become associated with all of these types of procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid arteries, cerebral vasculature, or neurovasculature, the release of emboli into the circulatory system can be extremely dangerous and sometimes fatal to the patient. Naturally occurring debris can also be highly dangerous to a patient. That is, debris which travels through the blood vessel as a natural result of bodily functions and not as a result of an intervention procedure. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments that naturally occur or that enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

In addition, the retrieval of fragmented clot may be incomplete, also resulting in emboli and distal occlusions, and further, access through tortuous lumens may prove difficult. Laser-based disruption devices employ the photo-acoustic effect to fragment clot. Local disruption may open up a proximal occlusion but also may cause significant distal emboli.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could otherwise cause problems to the patient's vasculature. Other techniques which have had some limited success include the placement of a filter or trap downstream from the treatment site to capture embolic debris before it reaches the smaller blood vessels downstream. However, there have been problems associated with conventional filtering systems as well. In particular, certain previously developed filtering devices do not optimize the area for embolic collection. That is, conventional filtering devices may not present a collection device that spans the entirety of the vessel or it may include supporting structure that itself impedes emboli collection. Certain other devices do not embody sufficient angular resistance to collapse.

Moreover, thrombectomy and foreign matter removal devices have been disclosed in the art. However, in addition to suffering from the same disadvantages as certain conventional filter devices, such devices have been found to have structures which are either highly complex such as with multiple components or highly convoluted geometry or lacking in sufficient or effective expansion and retraction capabilities. Disadvantages associated with the devices having highly complex structure such as with multiple components or highly convoluted geometry include difficulty in manufacturability as well as use in conjunction with micro-catheters. Other devices with less coverage can pull through clots due in part to the lack of experience in using the same or otherwise lack an expanded profile that is adequate to capture clots or foreign bodies.

Furthermore, in current interventional radiology practice, the need arises to remove a variety of objects from intraluminal spaces. Among these are embolic coils, guidewire tips, distal catheter segments, thrombus and other vascular emboli, few of which can be readily removed with current devices.

Thrombo-embolic materials can be friable, amorphous, and/or lubricious in nature contributing to this difficulty. Most current therapies rely on grasping, fragmenting, or dissolving the blood-based obstructions. Among the grasping devices are the loop snares and the wire basket snares. These devices may have limited effectiveness, due in part to the lack of encapsulation. Objects are difficult to grasp within these devices, and friable objects, e.g. blood-based blockages, tend to fragment when grasped or pulled, introducing multiple emboli.

Lytic drugs are also used to dissolve blood-based obstructions. These typically have the disadvantages of lengthy treatment/infusion times to remove the obstruction (>3 hrs.), production of emboli, and the potential for systemic iatrogenic bleeding as a side effect of the drug usage. Also, these drugs are not typically effective in removing obstructions that are not blood-based.

What has been needed is a reliable intravascular basket device and system for use when treating blood vessels. The basket devices should be capable of capturing any naturally occurring embolic debris or that which may be released into the bloodstream during an interventional treatment, while minimizing profile during delivery and maximizing coverage when deployed to safely contain the debris until the basket device is removed from the patient's vasculature. The devices should embody an expanded profile that presents a consistent radial opening that completely occupies the vessel at the repair site as well as structure for effectively resisting collapse. Moreover, such devices should be relatively easy to deploy and remove from the patient's vasculature and also should be capable of being used in narrow and very distal vasculature such as the cerebral vasculature. The following invention addresses these needs.

SUMMARY OF THE INVENTION

Briefly and in general terms, the present invention is directed towards a basket for removing undesired material or objects and restoring patency of blood vessels. The basket is a linked or monolithic framework of thin struts that is radially expansible. The basket of the present invention embodies a structure that provides a consistent radial opening as well as improved radial and angular resistance to collapse. That is, as the device is pulled such as through a vessel, the entrance thereto will not fall back or tip over. Moreover, the basket device maintains clearance in its interior space along its length allowing the material or objects to enter and be captured.

In one aspect of the invention, the basket includes struts with very small widths and thicknesses and rings with very small widths and thicknesses but large expansion ratios. It is particularly beneficial to manufacture the basket from a piece of tube stock, as opposed to prior art wire baskets, because the resulting basket is more ordered upon compression, returns to its expanded state more reliably and is quicker to manufacture. The body of the basket device is defined by a plurality of openings bounded by generally longitudinally and generally circumferentially extending members. A proximally extending member is attached to an elongate wire and the assembly is contemplated to be used in conjunction with a generally tubular delivery catheter. In this aspect the body provides enhanced stability at the proximal transition between the wire and the proximally extending members because the design may allow for varying lengths and widths of the proximally extending members. The basket may be manufactured from a single tubular element or from a sheet to form a desired configuration.

Overall, the intent of the invention is to provide a structure that has the capacity to engage, encompass and retain naturally occurring or foreign bodies while having a minimal profile that can traverse easily and repeatedly through a standard microcatheter across tortuous anatomy. The device embodies superior flexibility to be deployed and retrieved consistently across difficult anatomy while being able to retain captured material. The inner diameter of the device is heat-set to a pre-determined size. It is envisioned that there be a family of devices that have varying strut lengths, thicknesses, flexibility, and diameters as deemed appropriate for the specific type of vascular or non-vascular setting for which the device is to be used.

In a presently preferred embodiment, the basket device is self-expanding and includes a mid-section that forms a generally tubular profile. The proximally extending member projects as an axial extension of a line at the surface of the cylinder generally defining the substantially tubular portion to thereby provide an unobstructed opening at the proximal end of the basket. A terminal (i.e., distal) end of the basket device can be closed or constricted so as to form a pocket for receiving emboli or thrombotic debris.

The basket device can assume a number of forms. In one presently contemplated aspect, the basket device of the present invention embodies first and second end portions, and a mid-section having a plurality of consecutive rings, each ring having a plurality of generally straight members configured in an alternating V-pattern providing a plurality of proximal and distal apices. In another aspect, the intravascular basket device has a mid-section defined by a single ring also having generally straight members configured in an alternating V-pattern providing four apices on each of the mid-section proximal and distal ends. In yet another embodiment, the mid-section may embody a double ring design configured in a four apex pattern. In other aspects, the basket device mid-section may include rings having different lengths or, in the alternative, include a proximal section having different lengths. In the embodiments, the plurality of members can be curved, S-shaped, angled, tapered etc. rather than straight or can be a combination of straight and curved, angled, tapered or other combinations etc.

Moreover, the present invention embodies a tip for an endovascular device including an atraumatic soft coil for preventing damage to tissue and facilitates advanceability. The tip further includes multiple layers of coiled material to enhance these objectives as well as to provide stiffness variations.

These and other objects and advantages of the invention will become apparent from the following more detailed description, when taken in conjunction with the accompanying drawings of illustrative embodiments.

BRIEF DESCRIPTION OF THE DRAWINGS

FIG. 1 is a side view, partially in cross-section, of a vessel occluded by debris and a distal portion of a delivery catheter and intravascular snare assembly of the present invention positioned proximate the debris;

FIG. 2 is a side view, partially in cross-section, of the intravascular basket as deployed within the vessel of FIG. 1;

FIG. 14 is a perspective side view, depicting the device pattern projected onto the tubing which it will be cut from to produce the basket device of FIG. 3; and FIG. 15 is a perspective bottom view, depicting the device pattern projected onto the tubing which it will be cut from to produce the basket device of FIG. 3.

DETAILED DESCRIPTION OF THE PREFERRED EMBODIMENTS

Figure 3:
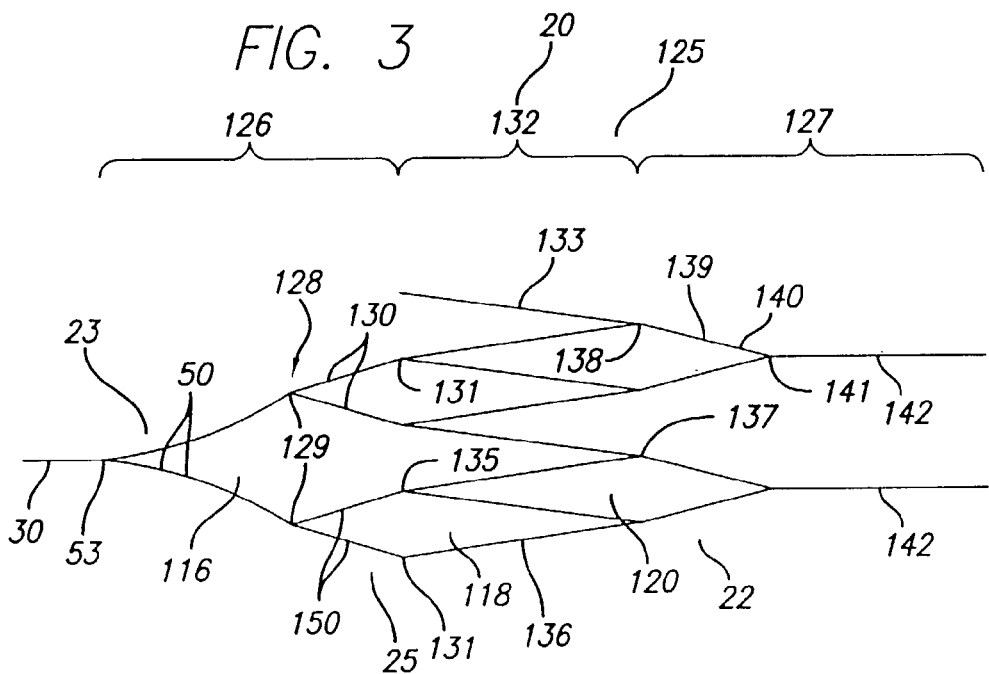
FIG. 3 is a plan view, depicting a pattern of a preferred embodiment of an intravascular basket of the present invention as if the basket was cut longitudinally and unrolled to show its pattern in a flat configuration.

Referring now to the drawings, and in particular FIGS. 1 and 2, there is shown a basket device of the present invention. The basket device 20 is adapted to provide more consistent and improved radial opening as well as enhanced angular resistance to collapse. Moreover, the basket device 20 of the present invention is configured to facilitate the maintenance of clearance in its interior space along its length allowing the material or objects to enter and be captured. Furthermore, since it is contemplated that the basket device 20 be manufactured from a tubular member to form elements with very small widths and thicknesses, the device is thus more easily packed to a relatively smaller diameter and inherently embodies high longitudinal flexibility.

The basket device 20 (FIG. 2) of the present invention includes a body 22 having a proximal end portion 24 and a distal end portion 26. The proximal end portion 24 is intended to be affixed to a terminal end portion of an elongate member 30 (i.e., wire; described in more detail below). In a presently preferred embodiment, the body 22 of the basket device 20 is generally tubular with a proximally directed opening 32 and a generally closed terminal end 34 to thereby form a basket for receiving embolus, stones, thrombus and foreign bodies found in vasculature or other body cavities.

The basket device 20 for intravascular uses is contemplated to be used in conjunction with a generally tubular delivery catheter 40, such as a microcatheter. Additionally, it is contemplated that a conventional guide catheter (not shown) be used in combination with the delivery catheter 40 loaded with a basket device 20. A guide catheter (not shown) is employed to provide a guide within a patient's vasculature through which the delivery catheter 40 is inserted. A proximal end of the guide may include a rotating hemostatic valve or "Y" adapter fitted with sealing hemostatic valves. The basket device 20 is intended to be self-expandable, however, it is possible to employ an expandable member such as a balloon catheter (not shown) to radially expand the basket device that is not self-expandable, but rather must be deformed to assume an expanded configuration.

In use, the body 22 of the basket device 20 is placed proximally in a compressed configuration coaxially within an internal bore of the generally tubular delivery catheter 40. The longitudinally extending elongate member 30 which is attached to the proximal end 24 of the body 22, is likewise coaxially received within the delivery catheter 40. Both the body 22 and elongate member 30 are slidable within the delivery catheter 40 and accordingly, the delivery catheter 40 and the basket device 20 can be displaced longitudinally with respect to each other.

A typical procedure will now be described. In order to restore patency in a vessel, the basket device/delivery catheter assembly 42 is introduced into a patient's vasculature using conventional means such as the Seldinger technique. Sometimes, a cutdown is made to gain access to the patient's vasculature. Using standard endovascular techniques, the emboli in the vasculature is located. The emboli is crossed with an appropriate guidewire (not shown) then the delivery catheter 40. If the vessel is occluded, contrast is injected distal to the occlusion to map the distal vessels. The tip 48 of the delivery catheter 40 is positioned one basket length or slightly more beyond the emboli. The guidewire is removed and the basket device 20 is loaded through a rear hub (not shown) of the delivery catheter 20 with the assistance of an introducer sheath (not shown). The basket device 20 is advanced 30–40 cm and the introducer sheath is then removed.

Next, the basket device 20 is advanced until the tip 26 of the basket is positioned at the distal end of the delivery catheter 40. Radioopaque markers are located on either side of the basket so that the operator can see when the basket is located just inside of the end of the delivery catheter 40. The basket device 20 is held in place by the operator holding the elongate member 30 still while the catheter 40 is retracted to allow the basket device to expand. Holding the basket device 20 in place, the catheter 40 is pulled back until it is proximal to the emboli 46. Then, the basket device is drawn back allowing the emboli 46 to enter the basket device 20. Alternatively, the entire system can be drawn back holding relative positions between the basket device 20 and the catheter 40. This step can be assisted with a "stuttering" technique where the basket device 20 is drawn out a small amount, perhaps 2 mm, then the elongate member 30 is advanced back perhaps 1 mm to allow the mouth of the basket device 20 to re-open fully, thereby assisting clot or emboli entry into the basket. Then the system is drawn out another 1 mm. This is repeated until the basket device 20 has traversed a distance about its own length. To reduce the risk of losing the material contained in the basket or device, blood flow control may be used during extraction. For example, a guiding catheter with a flow control device such as an elastomeric balloon at the distal tip may be employed to slow or stop blood flow past the device during retrieval.

If the emboli 46 is foreign in origin, such as a coil, the basket device 20 can be moved back and forth past the coil in an iterative attempt to engage the coil in the struts of the basket. When this has occurred, the catheter 40 can be advanced causing the basket to collapse and pinch the coil, locking it into one of the openings of the basket device 20. If the emboli is not radiopaque, its position may be checked by a contrast injection and noting a "filling defect." Also, the radiopaque tip 26 of basket device 20 can be observed under fluoroscopy during this process. A pulsing motion can indicate restored flow.

The system 42 is then drawn back until the distal end of a proximal device marker coil (described below) is at the tip of the guide. At this point, a large syringe, perhaps 60 cc, is attached to the guide catheter at the "Y" adapter on the hub. The guide catheter is aspirated as the basket device 20 and emboli 46 are drawn into the guide. Aspiration is maintained until the basket device 20 is fully into the "Y" adapter of the guide catheter, but the basket device 20 is not yet drawn through the hemostatic valve. The "Y" adapter is detached and removed with the basket device in it, allowing a moment of bleed back through the guide to flush any loose emboli. Optionally, then a second "Y" arm is attached to prevent excessive bleed back. The guide is then flushed with saline and the entire procedure repeated as required to remove further emboli.

The manner in which the body portion 22 of the basket device 20 self-expands within the vasculature and the resultant expansion profile provides a number of advantages. In particular, the body 22 expands to conform to the repair site 44. That is, the generally tubular profile of the body portion 22 substantially conforms to the walls defining the blood vessel 49. Alternatively, the basket device 20 can be sized such that upon full expansion it has a diameter smaller than the diameter of the blood vessel 49 if desired. Moreover, the expansion of the body 22 facilitates the maintenance of clearance in its interior space along its length allowing the material or objects 46 to enter and be captured and specifically provides a substantially unobstructed access to the proximally directed opening 32 to the body 22. Significantly, as the body 22 self-expands, members 50 and 51 leading to the opening 32 to the body 22 are angled or oriented so as to be adjacent to the walls defining the blood vessel 49 and are therefore substantially removed from the flow path to thereby provide an unobstructed opening 32.

In its expanded state, the basket device 20 is particularly well-suited to remove embolic or thrombotic debris 46 from the blood vessel 49. As stated, the basket device 20 can be withdrawn proximally so that the debris 46 can be captured by the body 22 of the basket device 20. Alternatively, a separate pusher mechanism (not shown) can be employed to push the debris 46 within the basket defined by the body portion 22. Once the debris has been captured, the system 42 can be removed from the patient's vasculature or the basket device 20 containing the debris 46 can first be pulled within the guide catheter (not shown) and then the assembly 42 removed from the target repair site 44. Also, just the proximal end portion 24 of the basket device 20 can be cinched down to lock the debris without being fully pulled into the delivery catheter 40.

It is to be understood, however, that thrombus or other blood-based material captured within the basket may be eliminated in a variety of ways. For example, the material may be drawn into the guide catheter with the aide of suction applied to the guide catheter, and removed from the body. Also, these materials may be removed from the occluded vessel and allowed to dissolve under natural or induced lytic processes. Alternately, the blood-based material may be inserted into other vasculature more tolerant of occlusion and released.

Figure 3A:
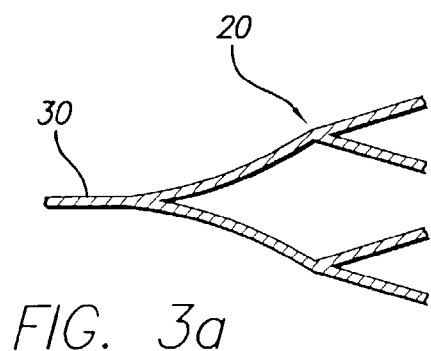
FIG. 3a is an enlarged view of a portion of an intravascular basket of the present invention, depicting curvilinear members defining the basket.
Figure 3B:
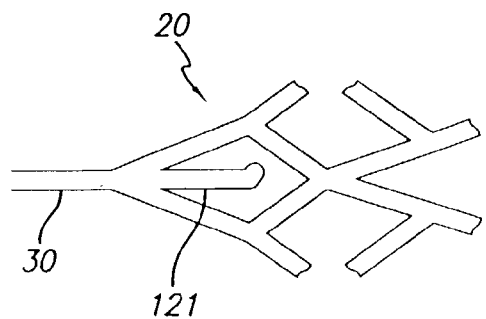
FIG. 3b is an enlarged view of a portion of an intravascular basket of the present invention, depicting a filler member positioned between other members defining the basket.

Referring to FIG. 3, in a preferred embodiment of a basket pattern 125 shown as if it was cut longitudinally and unrolled to depict its pattern in a flat configuration, a basket 20 includes a proximal section 126, mid-section 132, and a distal section 127. The sections 126, 132 and 127 together form a substantially tubular basket body 22 with a tapered distal end as will be developed further below. It is contemplated that the body 22 embodying such a pattern 125 be cut from a tubular member using a laser. Alternatively, the body can be made from a flat sheet of nitinol and rolled into a tubular basket body. As best seen in its flattened or unrolled state, the basket pattern 125 further includes an elongate member 30 extending proximally from a proximal end portion 53 of the basket body 22. It is also to be recognized that each of the members defining the basket body 22 in this or other embodiments may have curved, arced, S-shaped, partially straight sections or other configurations (See FIG. 3a, for eg.). Additionally, it is contemplated that the body can further include branches 121 with an enlarged or angled terminal end (FIG. 3b) which act as fillers between other members defining the body 20. Such fillers 121 aid in providing a basket highly equipped to contain material.

The proximal section 126 of the basket 20 includes a proximal end 23, a distal end 25 and a straight member section 128. The straight member section 128 includes a plurality of members 130 generally configured in a V-shape in that the members "fan out" or diverge in a distal direction. In this configuration, the straight members 130 lead to and aid in defining an opening 32 (see FIGS. 2 and 14) to the body 22, when in its as-cut tubular configuration. Therefore, the members 130 of the straight member section 128 are pair-wise configured in a V-shape such that two proximal vertices 129 are formed where the members 130 proximally merge and four open-ended distal end points 131 are provided to define the distal end 25 of the member section 128. It is noted that in the current configuration, the straight member section 128 defines the entirety of the basket proximal section 126, however, as will be subsequently discussed, in alternative embodiments, the proximal section 126 may include a plurality of straight member sections. Finally, the two proximal vertices 129 of the member section 128 merge into two curved members 50. The curved members 50 converge proximally to form a tab 53 that may be connected to an elongate member 30.

The mid-section 132 of the basket pattern 125 may be of a four apex design including a single ring 133 that defines the generally tubular mid-section 132. The ring 133 includes a plurality of straight members 136 configured in an alternating V-pattern forming a plurality of proximal apices 135 and distal apices 137. In order to achieve the four apex design of basket pattern 125, the ring 133 of the basket mid-section 132 may include eight straight members 136 converging end to end in an alternating V-pattern to form four proximal apices 135 and four distal apices 137. Each of the four proximal apices 135 merge into the open-ended distal end points 131 of the straight members 130 of the basket proximal section 126.

The intersection of the four straight members 130 of the basket proximal section 126 and the straight members 133 of the basket mid-section 132 at the proximal apices 135 define a plurality of diamond-shaped apertures 118. Additionally, a single enlarged diamond-like aperture 116, located substantially within the basket proximal section 126, is defined by the intersections at the proximal end of the basket proximal section 126 between the two curved members 50 and the proximal vertices 129 of the basket proximal section 126 and the intersections at distal end of the basket proximal section between the distal end points 131 of the proximal section 126 to the proximal apices 135 of the basket mid-section 132.

Referring still to FIG. 3, the distal section 127 of the basket 20 includes a single straight member section 139 having straight members 140 in a V-shape configuration that "fans-in" (i.e., converge) distally. At the proximal end, the straight members 140 include four open-ended proximal ends 138 (the branches of the V-shape) at the distal apices 137 of the basket 20 mid-section 132. At the distal end, straight members converge to form two vertices 141 at the distally directed members 142. The junction between the two straight members 140 of the basket distal section 127 and the straight members 133 of the basket mid-section 132 at the distal apices 137 define a plurality of diamond-shaped apertures 120.

The distally directed straight members 142 of the basket distal portion 127 may be joined together to form a substantially closed basket. This structure can be joined using soldering or by employing a coil (described herein below) that is wrapped about adjacent structures to form a soft tip. The distally directed extensions 142 may also be trimmed to a desired length.

Another way to describe the basket device is that it begins with a proximal elongate member linked to a series of divergent branches of increasing density covering successively smaller fractions of the tubular circumference. The increasing density of the divergent branches wrap around the circumference from the side where the elongate member ends to form the tube. Linked from the divergent branches is one or more ring segments in which an equal number of struts enter and exit at the joints. Branching from the ring segment is a series of convergent branches of decreasing density covering successively larger fractions of the tubular circumference. This section is tapered down to the distal tip to reduce the required coverage area thus maintaining adequately small openings for encapsulation.

It is noted that the dimensions of a basket pattern may be varied in a number of ways to produce a number of alternative embodiments of the current invention. From these alternative embodiments it will be understood that the lengths of the straight members of the mid-section rings may be varied accordingly to address any specific application requirement. Similarly, the lengths of the generally straight members of the member section of the proximal section may also be varied in length according to the desired design requirement. In order to have the device collapse evenly, all continuous (not recursive) paths from the first bifurcation to the last convergence of members must be of approximately the same length. Otherwise, during collapse the longer members are forced to buckle or the shorter members are forced to stretch to achieve a substantially linear constrained configuration.

Referring to FIGS. 4–7, alternative embodiments of the current invention are depicted. Generally, the basket patterns 145 include a mid-section 148 having two rings 152 and 153 configured in a "four apex" design. Each ring 152, 153 is defined by a plurality of connected vees to thereby define a ring having a generally serpentine pattern. A two ring design having a distal taper may provide enhanced clot capturing capabilities because of the smaller sized apertures located at the distal portions of the basket body 22. In the second and fourth embodiments (FIGS. 4 and 6), the rings 152 and 153 include straight members 155 and 159 having a first length. In the third and fifth embodiments (FIGS. 5 and 7), the rings 152 and 153 include straight members 170 and 174 having a second length that is longer than the first length of straight members 155 and 159. Therefore, the rings 152 and 153 of the second and fourth embodiments are shorter in length than the rings 152 and 153 of the third and fifth embodiments. It is envisioned that the length of the rings of the third and fifth embodiments may be two or more times longer than the rings of the second and fourth embodiments and that there can be any number of rings.

As with the previous embodiment described above, in all four alternative embodiments of basket pattern 145 (FIGS. 4–7), the straight members of each ring are configured in an alternating V-pattern layout to produce four apices on both the proximal and distal ends of each ring. Each ring 152 includes proximal apices 154 and distal apices 156 and each ring 153 includes proximal apices 158 and distal apices 160. The ring 152 is connected to ring 153 at the connection 157 between apices 156 and 158. Together rings 152 and 153 form the generally tubular mid-section 148.

Similar to the first embodiment (as shown in FIG. 3), the basket patterns 145 of the second through fifth embodiments (FIGS. 4–7) includes a proximal section 146 and a distal section 147 configured and connected to the mid-section 148 in a like manner as the first embodiment. As mentioned above, the two ring design of the basket patterns 145 allow for a distally tapering body 22 that provides for the capture of smaller emboli because the additional ring results in a body 22 having an increased number of apertures which are each smaller in size than those of the single ring design.

Figure 4:
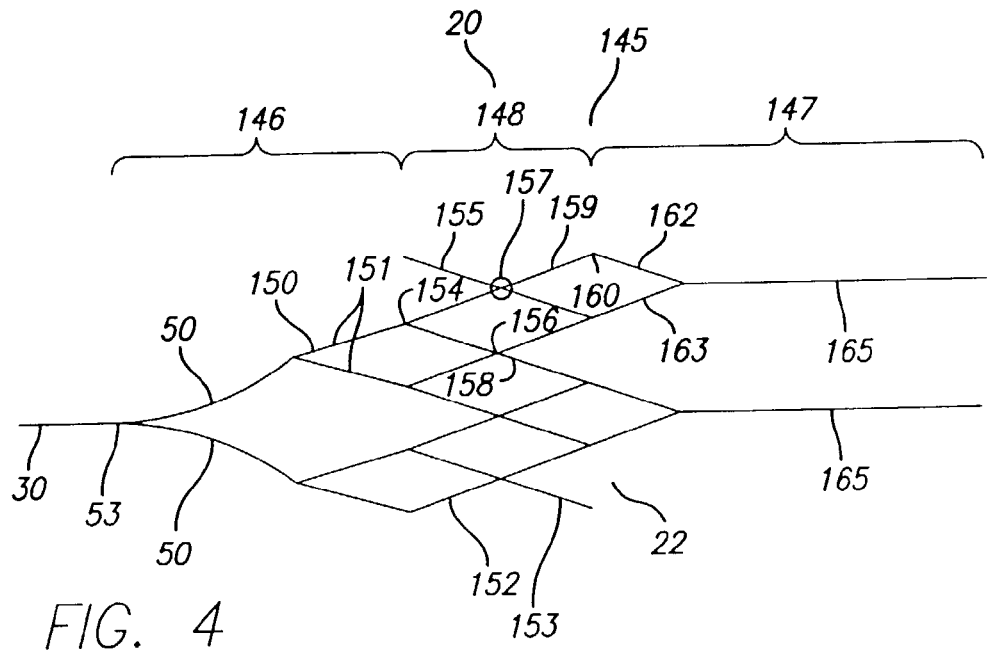
FIG. 4 is a plan view, depicting an unrolled pattern of a second alternative embodiment of an intravascular basket of the present invention.
Figure 5:
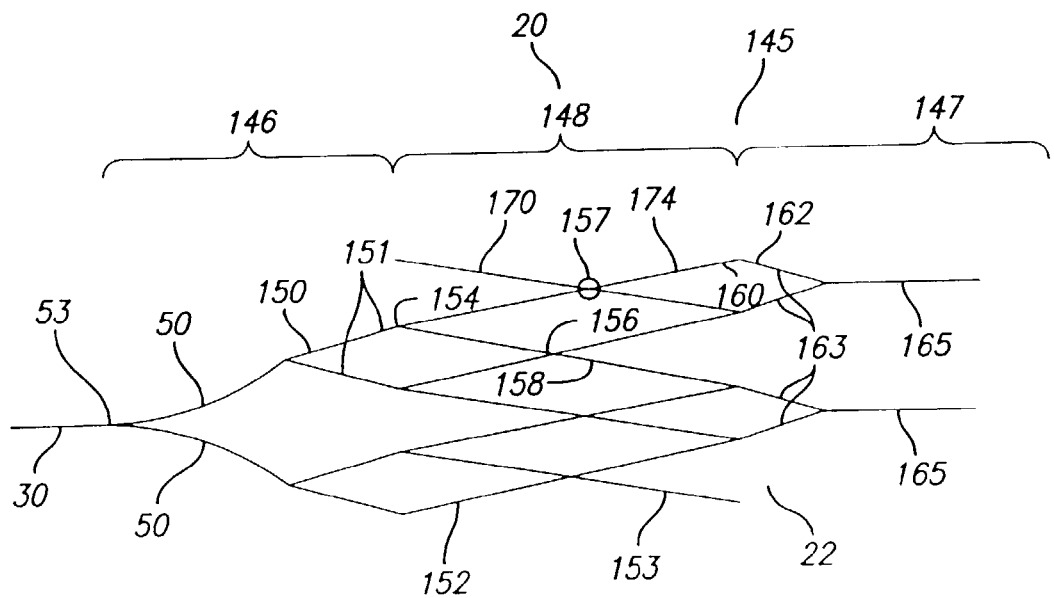
FIG. 5 is a plan view, depicting an unrolled pattern of a third alternative embodiment of an intravascular basket of the present invention.
Figure 6:
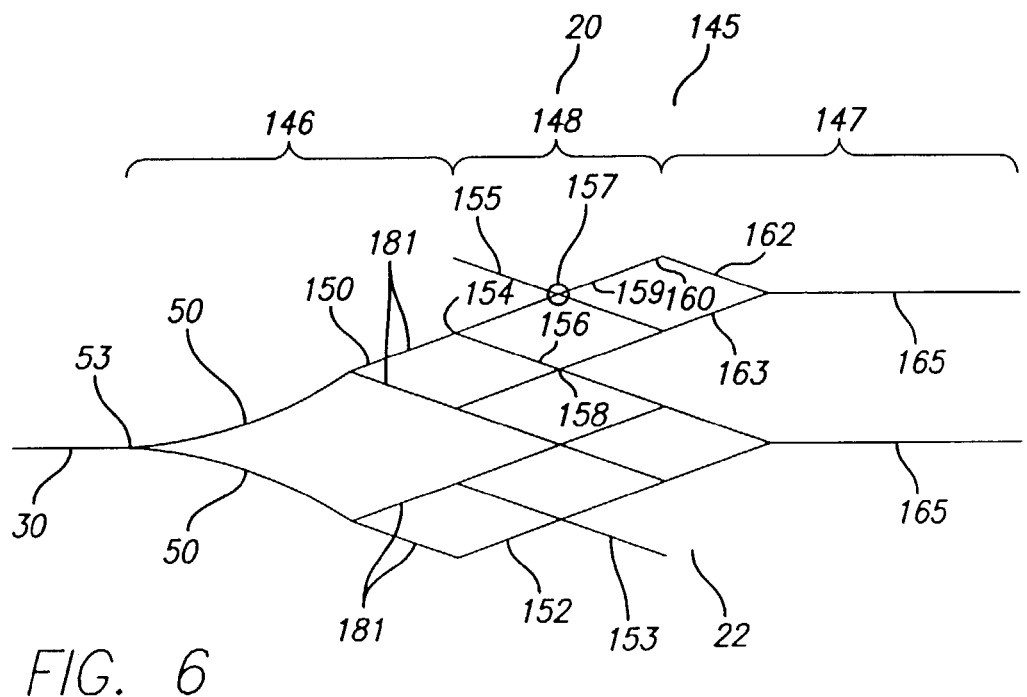
FIG. 6 is a plan view, depicting an unrolled pattern of a fourth alternative embodiment of an intravascular basket of the present invention.
Figure 7:
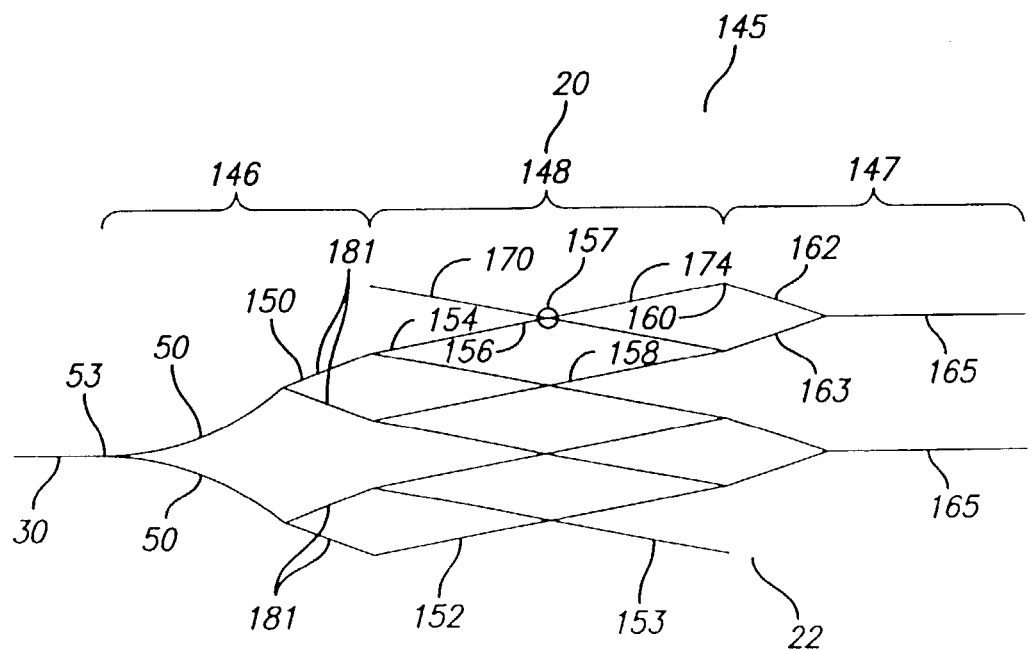
FIG. 7 is a plan view, depicting an unrolled pattern of a fifth alternative embodiment of an intravascular basket of the present invention.

Referring to FIGS. 6 and 7, further variations on the embodiments of FIGS. 4 and 5 respectively are provided. The variations include changes to the proximal transition defining proximal opening 32 of the basket 20. Therefore, in the second and third embodiments (FIGS. 4 and 5), a first member section 150 includes straight members 151 having a first length, while in the fourth and fifth embodiments (FIGS. 6 and 7) the first member section 150 includes straight members 181 having a second length that is shorter than the length of straight members 151. The change in the length of the members of the first member section 150 is intended to increase the radial strength of the device proximally. Therefore, the radial strength of the proximal transition of the device body 22 is increased which improves emboli capture by holding the device open and a shorter tab improves push by providing greater resistance to column buckling.

As can be seen from the various embodiments presented herein, the basket device 20 may be configured having different mid-section 148 or proximal section 146 lengths or may be designed to include different numbers of apices within the mid-section. These changes are only dependent on the design requirements of the physician, and any such modification will not depart from the scope of the present invention.

Figure 8:
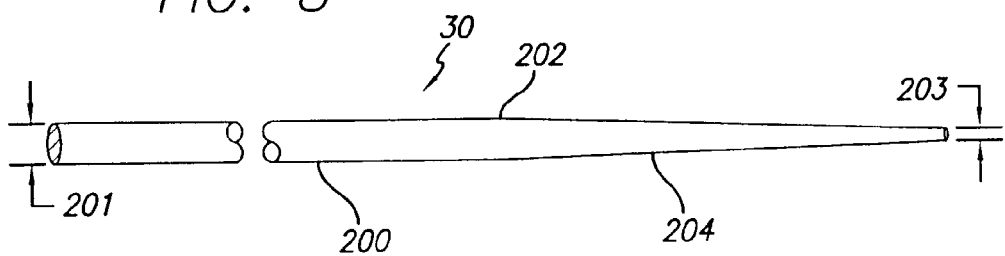
FIG. 8 is a plan view, depicting an elongate member of the present invention.

Referring now to FIG. 8, there is shown one preferred embodiment of the elongated member 30 of the present invention. The member 30 embodies a gradual or step-tapered core comprising a proximal section of 304V stainless steel and a distal section of nitinol or an equivalent material for the intended purpose. A proximal portion 200 of the member 30 has a generally constant cross-sectional profile and a first diameter 201. At a transition point 202, the member 30 begins to taper in a gradual and consistent, alternatively in a step-tapered or in parabolic or other non-linear manner, from the first diameter 201 to a second diameter 203 along a distal end portion 204.

Figure 9:
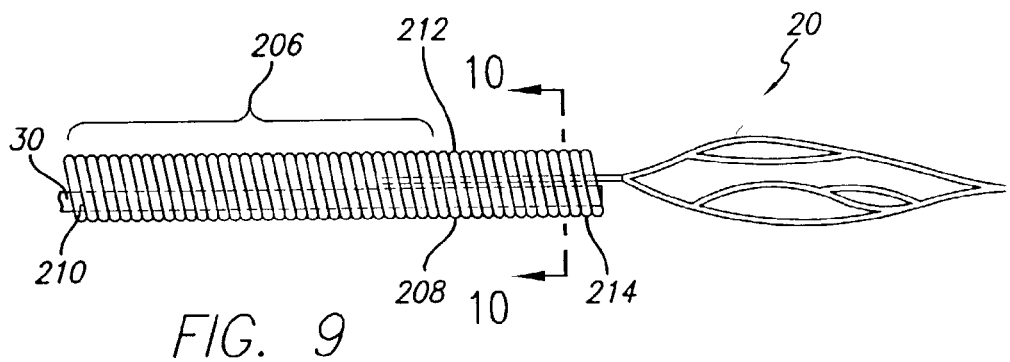
FIG. 9 is a side view, partially in cross-section, depicting a plurality of coils configured about a distal end portion of the elongate members in combination with a basket device of the present invention.
Figure 10:
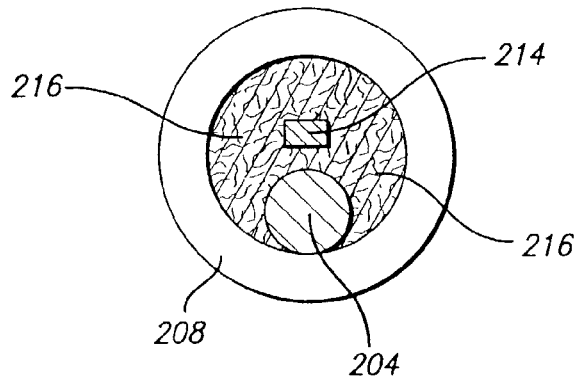
FIG. 10 is a cross-sectional view, depicting the assembly of FIG. 9 taken along lines 10—10.

As shown in FIGS. 9 and 10, a pair of longitudinally adjacent arranged coils 206, 208 are employed to attach a proximal tab 214 of a basket device 20 to the distal end portion 204 of the elongate member 30. The first, proximal coil 206 is contemplated to be composed of 304V stainless steel, the first coil being soldered to the elongate wire 30 near its tapered portion 210. The second coil 208 is contemplated to embody a medical grade radiopaque wire, typically a platinum alloy such as about 90% platinum and 10% iridium alloy. This second coil 208, which serves as a radiopaque marker, is soldered to the elongate member 30 near a distal end portion 212 of the first coil 206. Alternatively, the second coil 208 is soldered to the first coil 206. A proximal tab 214 of the basket device 20 is contained within the second coil 208 and is soldered 216 to the elongate member 30.

Figure 11:
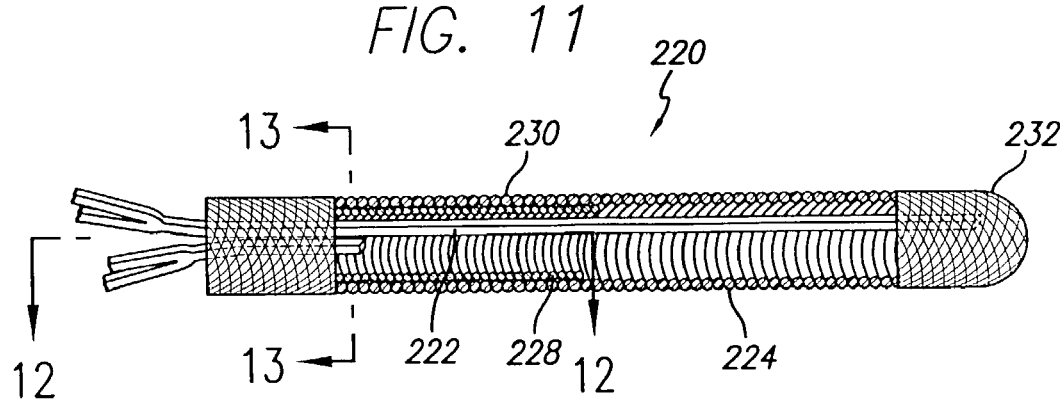
FIG. 11 is a side view, partially in cross-section, depicting a distal end portion of a tip of the basket device of the present invention.
Figure 12:
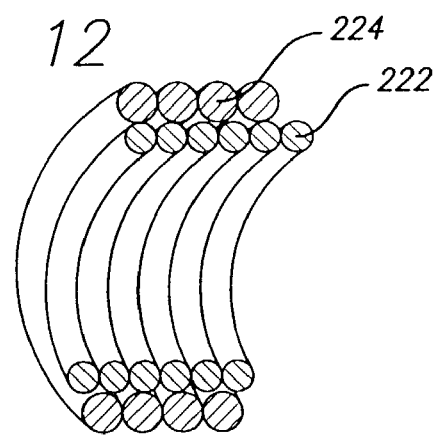
FIG. 12 is a cross-sectional view, depicting a portion of the assembly of FIG. 11 taken along lines 12—12.
Figure 13:
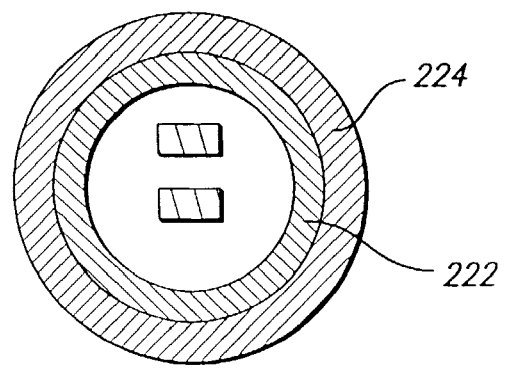
FIG. 13 is a cross-sectional view, depicting the assembly of FIG. 11 taken along lines 13—13.

Turning now to FIGS. 11–13, one presently preferred embodiment of a distal tip portion 220 of the basket device 20 of the present invention is described. The distal tip portion 220 embodies two partially coaxial coils 222, 224, the combination of which retains the distally directed extensions projecting from the body 22 of the basket device 20. The combination also provides a soft atraumatic tip with variable stiffness from softest distally to stiffer proximally. Varying the relative lengths of the tip and coils 222, 224 results in creating changes in stiffness and thus, can be selected to provide the device with desired flexibility.

The inner coil 222 is comprised of nitinol or equivalent material, and begins at a proximal location 226 and extends to a distal location 228. The nitinol inner coil 222 provides kink resistance as well as creates a smooth stiffness transition from the tip of the basket portion of the basket device 20. The outer coil 224 is coaxially configured about a distal portion 230 of the inner coil 222 and is preferably comprised of 90% platinum and 10% iridium alloy or an equivalent combination of materials. As such, the outer coil 224 can operate as a radiopaque marker.

The distal tip portion 220 further includes a rounded terminal end 232 that provides a blunt atraumatic surface. The terminal end 232 embodies a soldered joint which acts in retaining the helical configuration of the outer coil 224.

With reference to FIGS. 14 and 15, a brief summary of the process used to manufacture the basket devices 20 of the present invention is provided, with a specific focus on a second embodiment of the present invention. As shown in FIG. 3, the preferred embodiment of the present invention is relatively similar to the other embodiments disclosed and includes a four apex single ring pattern 125. It is contemplated that the basket devices 20 of the present invention be cut from a tube 240 using a laser. In particular, a specific pattern is programmed into the laser device and the laser is activated to cut the desired pattern into the tubular element 240. The excess tubular components are removed, thereby leaving a manufactured structure such as the basket pattern 125 shown in FIG. 3, corresponding to the desired pattern. In a presently preferred embodiment, a superelastic material such as nitinol is a material of choice for the basket device 20. Thereafter, post-processing such as surface treatment, burr removal, oxide removal and/or shape setting of the manufactured structure is performed. Heat treating is also performed for stress-relief of the device.

In particular, post-processing steps include taking an as-cut device and bead blasting the device with aluminum oxide blasting media. The device is then inspected under a microscope for residual slag. If slag remains, the device is bead blasted again. Thereafter, the device is stress relieved in a molten salt bath without expanding. The device is subsequently heat-expanded in a molten salt bath mounted on a suitable size mandrel. After heat expansion, surface oxidation is removed in an aqua regia bath. When nitinol is the material of choice, the nitinol is etched with HF solution to desired strut size resulting in desired softness. The device is then mounted on a guidewire using coils and solder.

In the case of the pattern 125, the post-processing may include deforming the pattern 125 and then joining together the distal end members 142 for the purpose of achieving a closed basket for receiving debris found in vasculature. Being so configured, the pair of diverging members 50 define an opening 32 to the resultant basket and the elongate member 30 extends from a sidewall defined by the opening.

The basket devices of the present invention each provide improved radial opening compared to prior art loop snares since in an expanded state, the elongate member 30 is positioned substantially out of the flow path. Additionally, the device embodies improved resistance to radial and axial loads compared to prior art loop snares. Moreover, since less deformation is required to produce a desired basket pattern, in that, angles between members are provided by laser cutting rather than from local deformations, for example, there is potentially improved stress distribution along the basket devices of the present invention compared to prior art loop snares. Additionally, a greater reduction in radial profile can be achieved without sacrificing performance and in particular, the device can be used in conjunction with microcatheters. As such, the basket devices 20 of the present invention can be passed through narrow and tortuous vasculature. The applications of the present invention are more widespread than that of conventional snare devices because of greater retrieval characteristics while retaining the deliverability characteristics.

The above described invention is principally conceived to be operational for use in engaging for the purpose of displacing and/or removing material either foreign or native to the body, including partial or complete obstructions embolic and/or thrombotic in nature, from intraluminal or extraluminal spaces of the body including but not limited to intravascular and/or intra-arterial regions of the cerebral vasculature, as well as tubings, stents, or other objects that may or may not be internal to the body. The purpose of the device is to restore functionality of the luminal space or systems dependent on the particular luminal space or as a method of producing any desired effect associated with the removal or displacement of undesirable material.

The intended delivery of the disclosed invention is by means of a commercially available catheter selected for its ability to access the desired location of engagement. The invention may be optimized for specific locations or uses by means of sizing the individual elements in the design and/or the overall dimensions, as well as selection of materials, mesh configuration, number and relative geometry of component members to meet the requirements of the operational space. Optimizations may include tabs protruding from the sides of members to increase coverage of the open areas between members, offsetting vertices of joints to increase packing efficiency, or providing unconnected distal curved path. There may additionally be variations of the dimensions of length, thickness, and width of distal and proximal tabs for joining basket with delivery wire and distal tip to provide smooth stiffness transitions from tip to basket and basket to delivery wire. Such optimizations are means of adjusting operational attributes including: flexibility, applied circumferential force, engagement effectiveness, deliverability and traversal through tortuous vasculature, and volume of material to be engaged.

Alternate or additional materials for the basket portion of the device may include a shape memory polymer thermoset, elastomer, thermoplastic constituents such as nylon, or other metal either pure or alloyed, as well as composite materials such as a combination of glass, aramid, or carbon in a binding matrix. A secondary mesh of the same or dissimilar material may be added to the basket. The wire portion of the device can alternatively be made from a single metal or combination of metals for kink resistance and high flexibility. Either or both components may be tapered to give a transition in stiffness that is appropriate for the vessel in which the invention is to be delivered. The distal tip of the device may incorporate concentric coils made of nitinol, stainless steel, or other metal or plastic to provide a soft flexible atraumatic end.

An alternate method of manufacture of the basket portion of the device may be photo etching, or metal or polymer injection molding or water jet cutting. Furthermore, the device may employ any combination of coatings, agents, or features including those that result from material addition or subtraction to create grooves, bumps, three dimensional patterns, and textures on inner and/or outer surfaces or any combination thereof to promote desired properties such as adherence of materials to be engaged, radiopacity, and low friction between the device and the vessel wall or microcatheter lumen.

In summary, the invention is deliverable to remote regions of the vasculature by gaining access through the use of a guidewire and microcatheter in the vasculature and subsequent deployment of the invention through the lumen of the microcatheter. In a vessel in which flow is impeded or obstructed by material and/or objects including those formed by the body such as blood clot, the device is deployed by withdrawing the microcatheter relative to the elongate wire and basket. Engagement occurs as the system composed of the invention is pulled proximal, causing the basket to encompass the material. After the material has been engaged, removal of the material is accomplished by withdrawing the system into a guide catheter lumen through which the microcatheter is passed with or without simultaneously pulling fluid through the guide lumen or removing the entire system with the guide catheter.

Thus, it will be apparent from the foregoing that, while particular forms of the invention have been illustrated and described, various modifications can be made without the parting from the spirit and scope of the invention. Accordingly, it is not intended that the invention be limited, except as by the appended claims.

What is claimed is:

1. A medical retrieval device for use in a patient's vasculature, comprising:
   an elongate member having a first end and a second end, the first end extending exterior of the vasculature;
   a body having a first section, a second section and a third section configured to form a basket, the body being attached to the second end of the elongate member;
   the body first section is a first end portion having at least one first member section;
   the body second section is a mid-portion having at least one ring member having a plurality of generally equal length members connected in an alternating V-pattern; and the body third section is a second end portion having at least one second member section.

2. The device of claim 1, the body further comprising an open first end and a substantially closed second end.

3. The device of claim 2, wherein the body is manufactured from a tube.

4. The device of claim 1, wherein the body has a longitudinal axis and is defined by a generally tubular sidewall, the elongate member extending from the sidewall in a parallel relationship with the longitudinal axis.

5. The device of claim 1, wherein the body has a compressed configuration and an expanded configuration.

6. The device of claim 1, the straight member section of the first end portion further comprising a plurality of straight or curvilinear members having proximal ends and distal ends.

7. The device of claim 6, wherein the straight or curvilinear members form a V-shape having converging vertices defining a proximal end and diverging branches defining a distal end.

8. The device of claim 1, the second section further comprising a plurality of straight members, the straight members forming a V-shape having diverging single branches defining a proximal end and converging vertices defining a distal end.

9. The device of claim 8, the second end portion further comprising a plurality of extending members, the extending members extend from the converging vertices of the distal end of the second section.

10. The device of claim 9, wherein the extending members are connected to form a distal tip to the body.

11. The device of claim 10, the distal tip further comprising a coil coaxially arranged about the extending members.

12. The device of claim 1, wherein the ring members include a plurality of apices defining a proximal end and a distal end, the apices are formed from the straight members merging in the alternating V-pattern.

13. The device of claim 1, wherein the first end portion further comprising a pair of the diverging undulate members, each of the undulate members having a first end and a second end, the first end of the undulate members converge to form a tab, the tab being affixed to the second end of the elongate member.

14. The device of claim 1, further comprising a generally tubular delivery catheter, the delivery catheter including an internal lumen sized to slidably receive the elongate member and the body.

15. The device of claim 1, wherein the device is fabricated from a tubular element using a laser.

16. The device of claim 1, wherein the device is made from self-expanding, superelastic, or shape memory material.

17. The device of claim 1, the body further comprising a distal tip portion.

18. The device of claim 17, the distal tip portion further comprising a blunt terminal end formed from a soldered joint.

19. The device of claim 1, further comprising a branch configured between pairs of diverging members defining the body.

20. The device of claim 19, the branch further comprising a length and a terminal end.

21. The device of claim 20, wherein the terminal end defines a pattern which is discontinuous from the length.

* * * * *